United States Patent [19]
Akiyama

[11] 3,941,678
[45] Mar. 2, 1976

[54] APPARATUS FOR ELECTROPHORETIC ANALYSIS

[75] Inventor: Junichi Akiyama, Kyoto, Japan

[73] Assignee: Shimadzu Seisakusho Ltd., Kyoto, Japan

[22] Filed: Feb. 20, 1975

[21] Appl. No.: 551,275

[30] Foreign Application Priority Data
Feb. 28, 1974   Japan................................ 49-23802
Mar. 7, 1974   Japan................................ 49-26961

[52] U.S. Cl........ 204/299 R; 204/180 R; 204/180 G
[51] Int. Cl.².......................................... B01K 5/00
[58] Field of Search............ 204/180 R, 180 G, 299

[56]   References Cited
   UNITED STATES PATENTS
3,533,933   10/1970   Strauch.......................... 204/180 G
3,649,498   3/1972   Pretorius et al. ............... 204/180 G
3,649,499   3/1972   Virtanen et al. ................ 204/180 R
3,705,845   12/1972   Everaerts ........................ 204/180 R
3,869,365   3/1975   Sunden ........................... 204/180 R

*Primary Examiner*—John H. Mack
*Assistant Examiner*—A. C. Prescott
*Attorney, Agent, or Firm*—Fidelman, Wolffe & Leitner

[57]   ABSTRACT

Apparatus for electrophoretic analysis of ions or like electrically charged particles, wherein the potential gradients of the different kinds of ions contained in a liquid column formed in an electrophoretic capillary tube are detected and the ratio between potential gradient of a selected one of said different kinds of ions and that of each of the other kinds of ions is calculated to obtain a value relating to the mobility of each of said different kinds of ions.

7 Claims, 6 Drawing Figures

APPARATUS FOR ELECTROPHORETIC ANALYSIS

This invention relates to an apparatus for electrophoretic analysis of ions or like electrically charged particles.

Isotachophoretic analysis is generally conducted in the following manner. A leading electrolytie, a terminal electrolyte and a sample solution between the two electrolytes are introduced into a capillary tube to form a liquid column therein, to which an electric field is applied along the length of the liquid column for separation of the component ions of the sample. In this case, if the ions or other electrically charged particles in the sample to be analyzed (which will be referred to simply as the ions) are cations, for example, the leading electrolyte contains a single kind of cations having a higher mobility than that of the sample ions while the terminal electrolyte contains a single kind of cations having a lower mobility than that of the sample ions.

The cations in the sample solution are separated as they migrate toward the cathode and when they have been completely separated, different zones are formed lying in the order of their respective mobilities and then these zones migrate at a constant speed. The width (that is, the thickness in the direction of migration) of each zone is proportional to the number of the ions contained therein. Therefore, by measuring the width of each of the completely separated zones it is possible to quantitatively determine the sample ions. The width of the zone can be measured by detecting the boundary between adjacent zones containing different kinds of ions.

Various types of detectors have hitherto been used for detecting the zone boundaries, such as those which depend for detection of the zone boundaries upon difference in absorption of ultra-violet rays by different zones or difference in the amount of heat pproduced due to the difference in the amount of heat produced due to the difference in the resistance between different zones, and those which are so designed as to detect the potential gradient along the liquid column in the capillary tube. The latter type, which is generally referred to as the potential gradient detector, has come to be in wide use due to its high sensitivity and versatility.

As is well known, in isotachophoresis the migration current is always at a constant level and determines the migration speed of the ion, so that so long as the migration current is kept at a constant level, the migration speed of the ion is kept constant.

On the other hand, the migration speed S of the ion can be expressed as the product of the inherent mobility M of the ion and the potential gradient V thereof as follows:

$$S = M \cdot V \tag{1}$$

If the speed S is constant, the above equation is expressed as:

$$M \cdot V = k \tag{2}$$

This means that the mobility is in inverse proportion to the potential gradient V.

Suppose that different kinds of ions contained in a sample have mobilities M1, M2, M3 ... Mn and potential gradient values V1, V2, V3, ... Vn, respectively, the following equation is obtained provided that the migration speeds of the ions are equal.

$$M1V1 = M2V2 = M3V3 \ldots = MnVn = k \tag{3}$$

From this equation we obtain $$\frac{V2}{V1} = \frac{M1}{M2}, \quad \frac{V3}{V1} = \frac{M1}{M3}, \quad \frac{V4}{V1} = \frac{M1}{M4}, \quad \frac{Vn}{V1} = \frac{M1}{Mn} \tag{4}$$

It is obvious from the equation (4) that the ratio of the potential gradient of one of the different kinds of sample ions to that of another kind is equal to the ratio of the mobilities of the two kinds of sample ions, and these values are independent of the migration speed. Therefore, if the potential gradients of the sample ions in the separated zones are measured so that with the potential gradient (e.g., V1 in equation (4)) of one particular kind of the sample ions being chose as a standard or reference, if the ratio of each of the potential gradients (V2, V3, ... and Vn) of the other sample ions to the standard value V1 is calculated, it is possible to obtain values related to the mobilities of the sample ions and from these values the sample components being measured can be identified.

Accordingly, the primary object of the invention is to provide an apparatus for electrophoretic analysis of samples, which is capable of obtaining a value relating to the mobility specific to each of the separated sample ions so that the sample ions can easily be identified. To this end, in accordance with the invention the potential gradient of a standard or reference ion and those of the sample ions are measured and the ratio of the potential gradient of each of the sample ions to that of the reference ion is calculated.

In one embodiment of the invention the apparatus comprises a first detector for detecting the potential gradient of a leading ion, a second detector for detecting the potential gradients of the different kinds of ions contained in a sample, the first and second detectors being arranged alongside the capillary tube in which isotachophoretic separation of the sample ions is to be effected, an operation circuit for performing a predetermined operation on the outputs from the two detectors to produce an output corresponding to the ratio of the potential gradient of each of the different kinds of sample ions to that of the leading ion; and an indicator for indicating the output from the operation circuit.

In another embodiment of the invention the apparatus comprises a detector for detecting the potential gradient of each of different kinds of ions, a circuit for storing the output from the detector corresponding to the potential gradient of a particular kind of ions, an operation circuit for the outputs from both the storing circuit and the detector to produce an output corresponding to the ratio of the potential gradient of each of the different kinds of ions to that of said particular kind of ions, and an indicator for indicating the output from the operation circuit.

As previously mentioned, the migration speed S of a certain kind of ions is given by the product of the mobility M and the potential gradient V thereof, that is, $S = M \cdot V$. Therefore, the mobility M can be expressed as $$M = S/V \qquad (5).$$

If the migration speed and the potential gradient of a sample ion are measured, it is possible to calculate the mobility specific to the ion and consequently identify the ion.

Another object of the invention is, therefore, to provide an apparatus for electrophoretic analysis of ions or like charged particles, which is capable of directly obtaining the mobility of a sample ion immediately after it has been separated, so that the sample ion can be identified. To this end the apparatus of the invention comprises a detector for detecting the potential gradient of each separated ion to produce a corresponding output signal, a detector for detecting the migration speed of the ion to produce a corresponding output signal, an operation circuit for conducting a predetermined operation on the outputs from the detectors to produce a corresponding output signal, and an indicator for indicating the output from the operation circuit.

The invention will be explained in detail with reference to the accompanying drawings, wherein.

Figure 1:
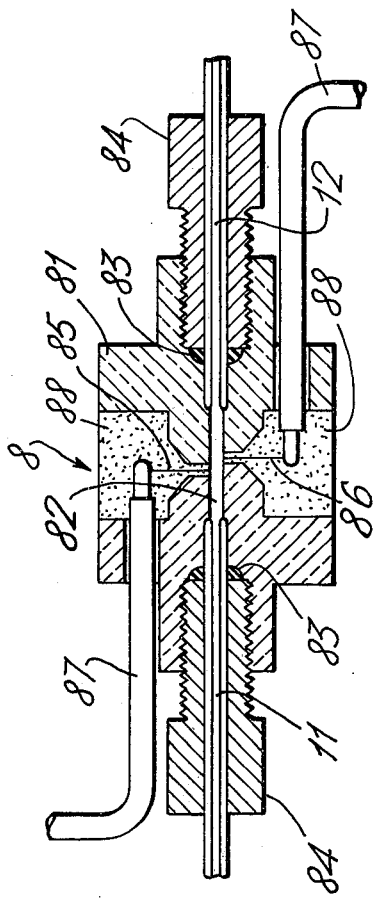
FIG. 1 is a schematic view of an apparatus for electrophoretic analysis.

Referring in detail to the drawings, first to FIG. 1, there is shown a capillary tube 1, which is made of an insulating material such as Teflon. The inner and outer diameters of the tube are, for example, 0.5 mm and 2 mm, respectively. A chamber or cell 2 enclosing a terminal electrode 21 is connected to one end of the capillary tube, to the other end of which another chamber or cell 3 enclosing a leading electrode 31 is connected. The two electrodes 21 and 31 are connected through lines 41 and 42 to the negative and positive output terminals of a source of electricity 4, which may comprise a current stabilized power supply which provides an adjustable constant output direct current, with a neutral tap being preferably grounded.

A pair of conduits 51 and 52 connect the terminal and leading electrode chambers 2 and 3 to a pair of tanks 54 and 53, respectively, adjacent the bottom portions thereof, which contain terminal and leading electrolytes, respectively. Stop valves 57 and 58 are inserted in the conduits 51 and 52 to control the supply of the electrolytes from the tanks 53 and 54 to the chambers 2 and 3. A pipe 55 connects the upper portions of the tanks 53 and 54 to a sourse 56 of presurized inert gas such as helium.

The capillary tube is provided with a sample introducing device 22 through which a leading electrolyte are introduced into the capillary tube to form a liquid column therein in the well known manner.

A heating chamber 7 encloses the capillary tube 1 to keep the liquid column at a predetermined temperature, which is controlled by a source of electricity 71.

Figure 2:
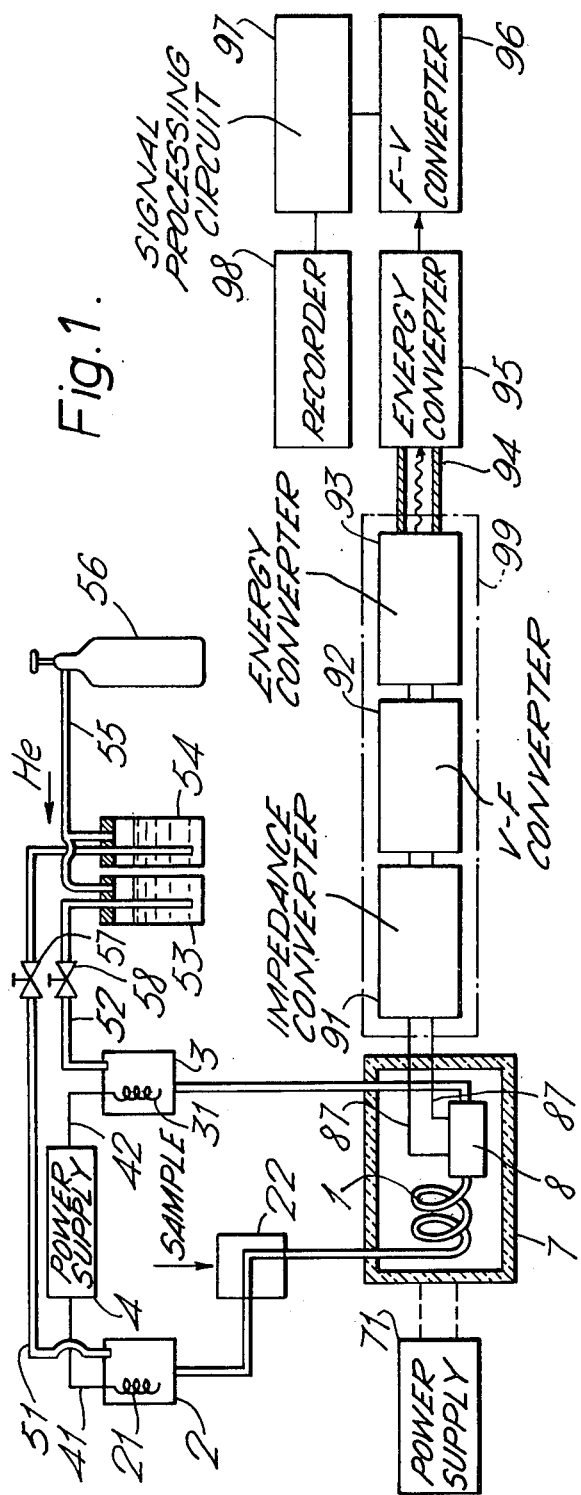
FIG. 2 is a sectional view of a potential gradient detector used in the apparatus of FIG. 1.

Adjacent one end of the capillary tube there is provided a detector 8, one example of which is shown in FIG. 2 as a potential gradient detector. The detector comprises a holding block 81 made of a transparent insulating material such as methacrylic resin, and along the axis of the block 81 there is provided a hollow cylindrical detecting chamber 82 having its opposite ends connected to the end portions 11 and 12 of the capillary tube 1.

The end portions of the tube are secured to and supported by the block 81 by means of screw plugs 84 with a seal tape 83 sealing between the adjacent members. A pair of electrodes 85 and 86 for detecting the potential gradient, made of a platinum wire having a diameter of about 0.08 mm, extend normal to the axis of the detecting chamber through a pair of holes formed in the block 81 as far as the inner ends of the electrode wieres are expposed at, but not projecting from, the inner surface of the detecting chamber 82, with the other ends of the electrodes being soldered to the bare ends of cable wires 87 held by the block 81. The space about the electrodes and the bare ends of the cable is filled with a suitable insulating adhesive material 88 such as Araldite (a trademark of CIBA).

It should be noted as the important features of the detector shown in FIG. 2 that, firstly, the inner diameter of the detecting chamber 82, e.g. 0.8 mm, is somewhat greater than that of the capillary tubes 11 and 12, e.g. 0.5 mm and, secondly, the electrodes 85 and 86 comprise as thin wires as possible the inner ends of which do not project into the detecing chamber 82 but agree with the inner wall surface thereof.

Due to the first feature the current density becomes lower in the detecting chamber than in the capillary tubes 11, 12 and due to the second feature the area of the electrodes which is in contact with the liquid in the detecting chamber is minimized so that discharge of the ions at the electrode surface and consequent formation of bubbles and attachement of deposits to the electrodes can be suppressed to a great extent.

Returning to FIG. 1, the sensing electrodes 85 and 86 are connected through a pair of cables 87 to an impedance converter 91 having a high input impedance and a low output impedance. The output of the impedance converter 91 is applied to a voltage-to-frequency converter 92 which produces a pluse signal the frequency of which is proportional to the output of the impedance converter 91. A first energy converter 93 such as a light emitting diode receives the output electrical signal from the converter 92 to convert it to a corresponding optical or other electromagnetic wave signal. A channel 94 transmits the electromagnetic wave from the first energy converter 93 to a second energy converter 95 such as a phototransistor or phototube which converts the optical signal again to a corresponding electrical pulse signal. The electrical signal is applied to a frequency-to-voltage converter 96 which produces a voltage corresponding to the frequency of the electrical signal received from the converter 95.

The output from the frequency-to-voltage converter 96 is applied to a signal processing circuit 97 including a differentiator and other elements not shown, the output from which is applied to a recorder 98, which may be replaced by an indicator, a displayer or any other suitable device for measuring the zone width.

An insulating means 99 isolates the circuits 91, 92 and 93 from the ground so as to prevent any leakage current from flowing between the sensing electrodes and the ground. The arrangement helps completely isolete the sensing portion from the fixed potential source such as the ground so that no leakage current flows between the sensing electrodes and the exterior parts thereby preventing formation of bubbles.

In operation, a leading electrolyte, a sample solution and a terminal electrolyte are introduced into the capillary tube, with the sample being interposed between the two electrolytes. When the output from the source 4 is impressed across the electrodes 21 and 31, a potential gradient is produced along the liquid column formed in the capillary tube 1, so that the ions, say, anions in the sample migrate toward the positive electrode 31.

The different kinds of anions in the sample are gradually separated into different zones according to their inherent mobilities as they move at their respective migration speeds which are betwwen the migration speed of the anions of the leading electrolyte and that of the anions of the terminal electrolyte. When the separation has been completed, each of the separated zones includes a different single kind of ions contained in the sample and the widths of the zones are proportional to the amounts of the sample ions introduced. After that the zones move at the same speed.

Figure 3:
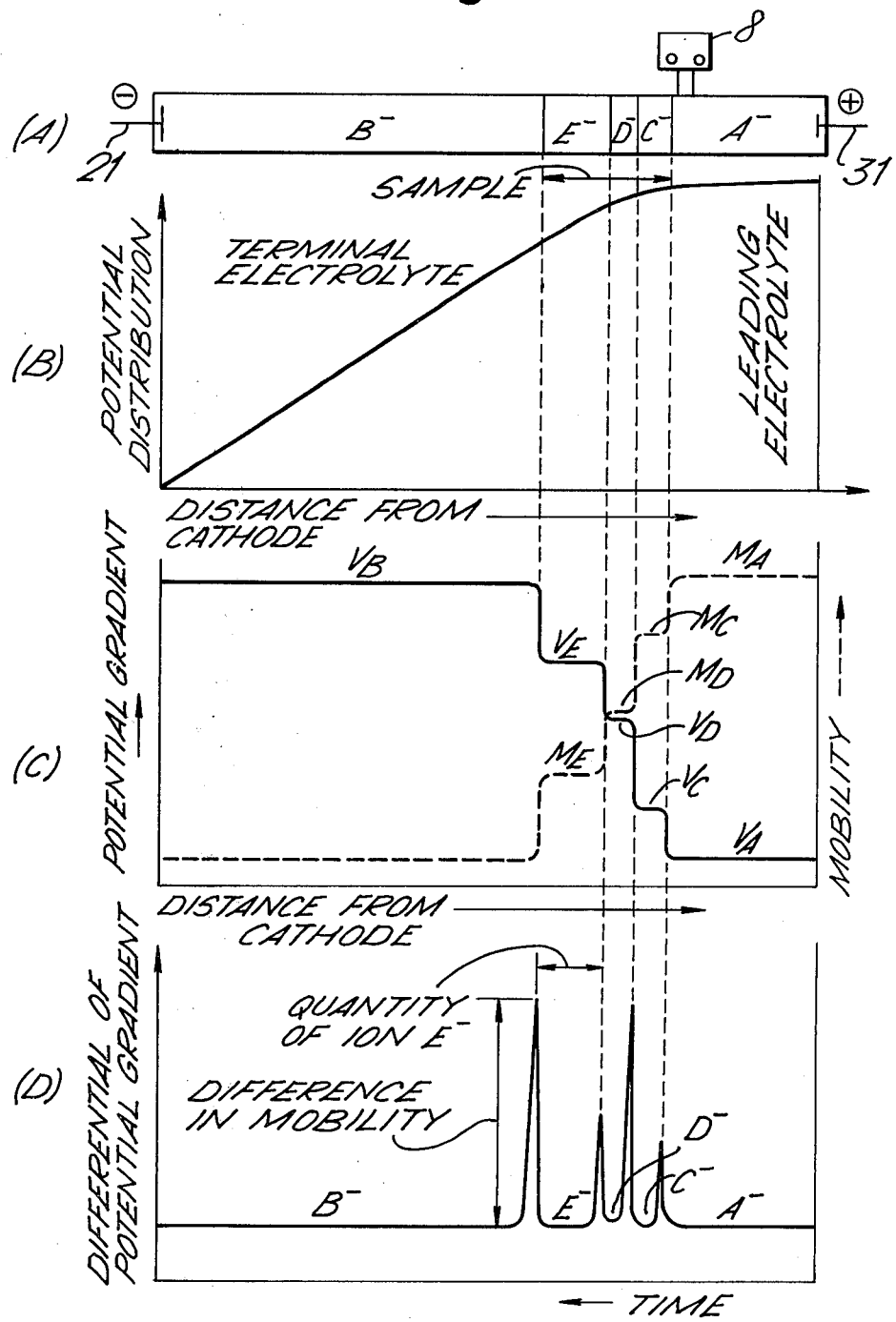
FIG. 3A is a schematic representation of separated ions in a capillary tube.
FIG. 3B shows the potential distribution along the capillary tube.
FIG. 3C shows the potential gradients and mobilities of the separated ions.
FIG. 3D shows the differentiated values of the potential gradients.

FIG. 3A schematically shows the zones completely separated in the above manner. In FIG. 3A the symbols + and − designates the polarities of the voltage impressed across the liquid column in the capillary tube; the numeral 8 designates the potential gradient detector; and the symbols $A^-$ and $B^-$ designate the leading and the terminal ions, respectively, with different kinds of sample ions $C^-$, $D^-$ and $E^-$ in the separated zones between the leading and the terminal electrolytes.

FIG. 3B shows the potential distribution of each ion in the capillary tube at a time corresponding to the separated condition shown in FIG. 3A, and FIG. 3C shows the potential gradient values VA, VB, VC and VE and mobilities MA, MC, MD and ME of the ions. This means that the potential gradient values detected by the detectors 8 as the separated zones pass the detector one after another will draw the same curve as shown in FIG. 3C provided that the capillary tube has a sufficient length between the sample introducing device 22 and the detector 8 for the sample ions to be completely separated.

If the output from the detector 8 is differentiated so that the differentiated signal is plotted aginst time, a graph as shown in FIG. 3D is obtained. By the distance between adjacent differentiated signal peaks it is possible to know the width of each zone and consequently determine the quantity of each component of the sample, and by the difference in height between adjacent peaks it is possible to known the presence of a difference in mobility between the sample ions in adjacent two separated zones. However, these informations can be obtained only after the data on the recorder chart have been analyzed, and such analysis requires somewhat troublesome work.

According to this invention, the ratio of the potential gradient of each sample ion to that of a specific or reference ion is calculated, and directly from the ratio the sample ion can be identified.

Figure 4:
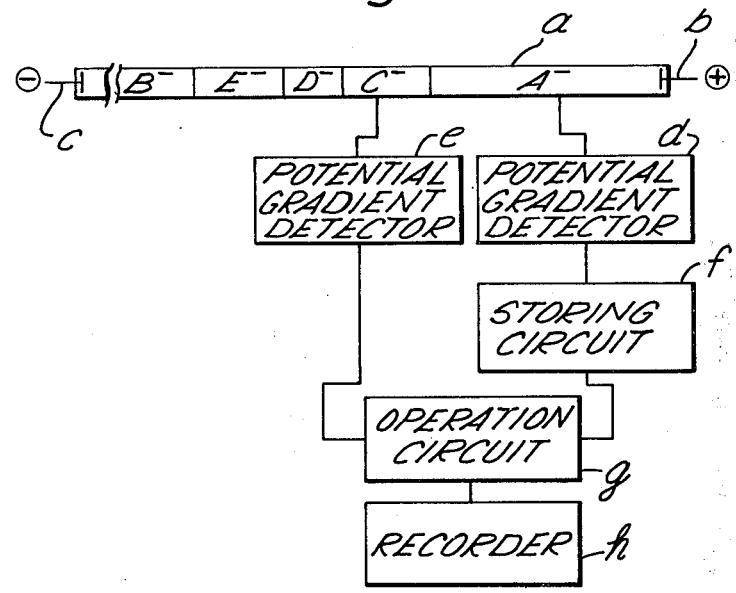
FIGS. 4 to 6 are schematic views of different embodiments of the apparatus of the invention.
Figure 5:
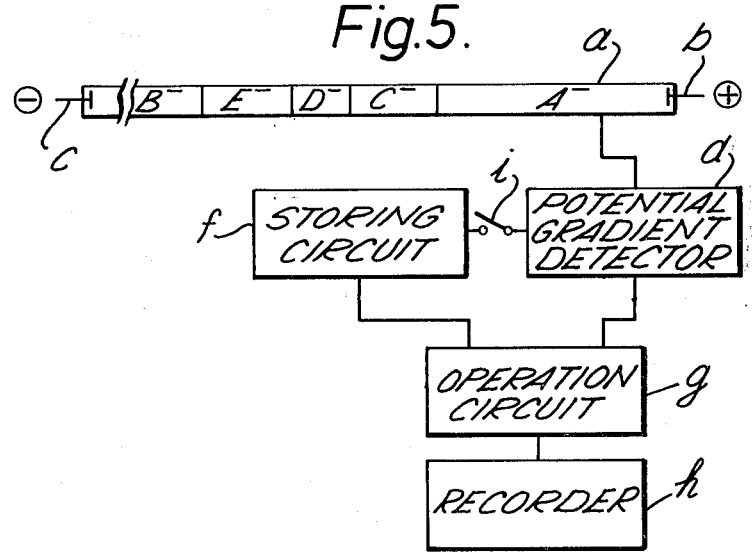

FIGS. 4 and 5 schematically show different embodiments of the invention. First in FIG. 4 a pair of electrodes $b$ and $c$ apply a constant current to an electrophoretic capillary tube $a$, within which leading ions $A^-$ and terminal ions $B^-$ and three different kinds of sample ions $C^-$, $D^-$ and $E^-$ now completely separated migrate at a constant speed toward the anode $b$.

A pair of first and second potential gradient detectors $d$ and $e$ are provided on the capillary tube, the detector $d$ being at the side of the anode and the detector $e$ being at the side of the cathode. The two detectors detect the potential gradients of the ions $A^-$, $C^-$, $D^-$ and $E^-$ to produce corresponding output signals. A storing circuit $f$ is connected to the output of the detector $d$ to store the detected potential gradient of the leading ion $A^-$. An operation circuit $g$ is connected to the output of the storing circuit $f$ and that of the second detector $e$ to calculate the ratios VC/VA, VD/VA and VE/VA, wherein Va is the potential gradient of the leading ion $A^-$ and VC, VD and VE are those of the sample ions $C^-$, $D^-$ and $E^-$.

As previously mentioned, these ratios are equal to the ratios of the mobility MA of the leading ion $A^-$ to those MC, MD and ME of the sample ions $C^-$, $D^-$ and $E^-$, that is, MA/MC, MA/MD and MA/ME, respectively. Since the ratios VC/VA, VD/VA and VE/VA are constant regardless of the measuring conditions such as the migration current, the diameter of the capillary tube, the concentrations of the electrolytes, etc., each of the ratios VC/VA, VD/VA and VE/VA expresses a value specific to the corresponding component ion of the sample.

Therefore, by indicating these values on a recorder or indicator h it is possible to obtain values relating to the mobilities specific to the sample components.

Turning to FIG. 5 which shows another embodiment of the invention, and wherein the same reference numerals denote corresponding parts, a potential gradient detector $d$ detects the potential gradients of the leading ion $A^-$ and the sample ions $C^-$, $D^-$ and $E^-$ succesively, and a storing circuit $f$ is connected through a switch $i$ to the detector $d$ so as to store the potential gradient VA of the leading ion $A^-$. An operation circuit $g$ is connected to the output of the storing circuit $f$ and that of the detector $d$ so as to calculate the ratios VC/VA, VD/VA and VE/VA of the potential gradients VC, VD and VE of the sample ions successively detected by the detector $d$ to the potential gradient VA of the leading ion.

In the above description, the ratio of the potential gradient of each sample ion to that of the leading ion is calculated, but the arrangement may be such that one of the different kinds of sample ions is chosen as the standard or reference ion and the ratio of the potential gradient of each of the other kinds of ions to that of the reference ion is calculated.

The following table shows the results of an experiment conducted in accordance with the invention. Chloride ion is used as the leading ion and chosen as the standard or reference and the ratios of the potential gradients of the other ions to that of the reference ion are obtained, while the inverse ratios of the mobilities of these ion are obtained theoretically from the mobilities of the ions. The migration current is 100 $\mu A$ and the pH is 6.0.

| | Ratios of potential gradients | Inverse ratios of mobilities (theoretical values |
|---|---|---|
| Chloride ion | 1.00 | 1.00 |

| -continued | | |
|---|---|---|
| Sulphate ion | 1.20 | 1.30 |
| Nitrate ion | 1.35 | 1.39 |
| Oxalate ion | 1.50 | 1.45 |
| Formate ion | 1.90 | 1.82 |
| Citrate ion | 2.10 | 1.99 |
| Maleinate ion | 2.50 | 2.42 |
| Acetate ion | 4.10 | — |
| Gultamate ion | 8.00 | — |

As shown in the table, the ratios of the potential gradients are slightly different from the inverse ratios of the mobilities although theoretically these two ratios must be equal.

The cause for the discrepancy may be due to errors in the experiments which have been caused by the low precision of the measuring device or by the fact that the mobility of each ion, unlike its atomic or molecular weight, considerably varies with the pH of the solution, the ambient temperature and other measurement conditions. However, the discrepany is negligible in practice in identification of various ions and can be reduced by improving the precision of the measuring device.

Figure 6:
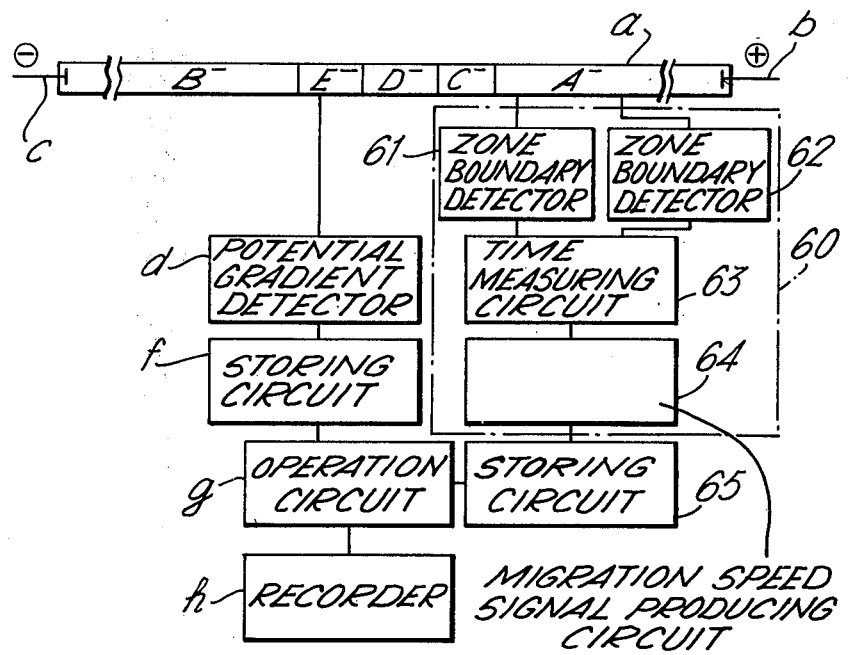

FIG. 6 schematically shows a third embodiment of the invention for directly obtaining the mobility of each separated sample ion from the potential gradient and the migration speed thereof. In FIG. 6 the same reference symbols as in FIGS. 4 and 5 denote corresponding parts so that explanation of these parts will be omitted.

In addition to the potential gradient detector $d$, the capillary tube $a$ is provided with a migration speed detector generally designated by 60. The detector 60 comprises: a pair of zone bundary detectors 61 and 62 arranged a predetermined distance apart from each other along the length of the capillary tube; a time measuring circuit 63 controlled by the output signals from the detectors 61 and 62; and a migration speed signal producing circuit 64 which receives the output from the time measuring circuit 63 to produce an output signal corresponding to the migration speed of the ion that has passed the zone boundary detectors 61 and 62. The migration speed signal from the circuit 64 is stored in a storing circuit 65.

The output from the potential gradient detector $d$ is stored in a storing circuit $f$, the output from which and the migration speed signal from the storing circuit 65 are applied to an operation circuit $g$ which conducts the calculation of S/V to produce an output signal corresponding to the mobility M of the ion. The signal expressing the mobility of the ion is indicated by recorder or indicator $h$.

In operation, the potential gradient detector $d$ detects the potential gradient of one of the separated ions after another as they move through the capillary tube toward the anode, and the detected potential gradient values are successively stored in the storing circuit $f$.

On the other hand, if the zone boundary detectors 61 and 62 are so designed as to produce an output in response to a change in the potential gradient, when the boundary between the zone containing the $A^-$ ions and the zone containing the $C^-$ ions passes the detector 61, this detector produces an output pulse whereupon the time measuring circuit 63 is started to produce an output signal until the same boundary passes the detector 62, whereupon the detector 62 produces an output pulse to terminate the output from the time measuring circuit 63. In response to the output from time measuring circuit 63, the circuit 64 calculates the migration speed of the ions $C^-$ to produce a corresponding signal.

Since the different kinds of ions have the same migration speed, the migration speed signal is stored in the storing circuit 65, so that from this migration speed and each of the potential gradient values of the different kinds of ions the mobility specific to each of the different kinds of ions is calculated and then indicated on the indicator $h$.

As mentioned just above, since the different kinds of ions have the same migration speed, if the time required for the boundary between the zones of the $A^-$ and $C^-$ ions to move from one of the two zone boundary detectors to the other is measured and memorized, it is not necessary to detect the migration speed again.

Various modifications and changes of the arrangements of the invention are possible. For example, in FIG. 6 the storing circuit $f$ may be omitted; and one of the two zone boundary detectors may be replaced by the potential gradient detector.

What I claim is:

1. Apparatus for electrophoretic analysis of ions and like electrically charged particles comprising: a capillary tube; means for providing within said tube a liquid column containing different kinds of ions; means for providing a potential difference between the opposite ends of said liquid column to separate said ions into different zones; means for detecting the potential gradients of said ions in said separated zones; and operation circuit means for calculating the ratio between the potential gradient of one of said different kinds of ions and that of each of the other kinds of ions.

2. The apparatus of claim 1, further including means for indicating the output from said operation circuit means.

3. The apparatus of claim 2, wherein said liquid column comprises a leading electrolyte containing leading ions, a terminal electrolyte containing terminal ions and a sample solution containing a single or different kinds of ions and interposed between said leading and terminal electrolytes.

4. The apparatus of claim 3, wherein said detecting means comprises a first detector for detecting the potential gradient of said leading ions and a second detector for detecting the potential gradient of each of said sample ions; and wherein said operation circuit means calculates the ratio of the potential gradient of each of said different kinds of sample ions to that of said leading ions.

5. The apparatus of claim 1, further including means for storing the potential gradient of a particular one of said different kinds of ions detected by said detecting means, and wherein said operation circuit means calculates the ratio between the potential gradient of said particular one kind of ions to the potential gradient of each of the other kinds of ions.

6. Apparatus for electrophoretic analysis of ions and like electrically charged particles, comprising; a capillary tube; means for providing within said capillary tube a liquid column containing different kinds of ions; means for producing a potential difference between the opposite ends of said liquid column to separate said ions into different zones; means for detecting the potential gradients of said different kinds of ions; means for detecting the migration speed of at least one of said different kinds of ions; operation circuit means for performing a predetermined operation on the outputs from said potential gradient detecting means and said migration speed detecting means to produce an output corresponding to the mobility of each of said different kinds of ions; and means for indicating the output from said operation circuit means.

7. The apparatus of claim 6, wherein said liquid column comprises a leading electrolyte containing leading ions, a terminal electrolyte containing terminal ions and a sample solution containing a single or different kinds of ions and interposed between said leading and terminal electrolytes.

* * * * *